United States Patent [19]

Elmi

[11] 4,278,655

[45] Jul. 14, 1981

[54] ANTIPERSPIRANT COMPOSITION

[75] Inventor: Steele J. Elmi, Midland Park, N.J.

[73] Assignee: Finetex, Inc., Elmwood Park, N.J.

[21] Appl. No.: 18,250

[22] Filed: Mar. 7, 1979

[51] Int. Cl.$^3$ .......................... A61K 7/32; A61K 7/38
[52] U.S. Cl. ...................... 424/47; 260/410; 260/410.5; 260/410.9 R; 424/66; 424/68; 424/184
[58] Field of Search ............ 424/47; 260/410.5, 410.9, 260/410

[56] References Cited

U.S. PATENT DOCUMENTS

| | | | |
|---|---|---|---|
| 970,662 | 9/1910 | Sulzberger | 260/410.5 |
| 2,428,450 | 3/1944 | Eitelman | 260/410.9 |
| 3,506,704 | 4/1970 | Miller et al. | 260/476 |
| 3,929,986 | 12/1975 | Bouillon et al. | 424/68 |
| 3,984,535 | 10/1976 | Ghilardi et al. | 424/70 |
| 3,998,788 | 12/1976 | Rubino | 424/68 |
| 4,065,564 | 12/1977 | Miles, Jr. et al. | 424/68 |
| 4,073,880 | 2/1978 | Pader et al. | 424/68 |
| 4,083,956 | 4/1978 | Shelton | 424/68 |
| 4,107,192 | 8/1978 | Bailey et al. | 260/410.5 |
| 4,113,852 | 9/1978 | Kenkare et al. | 424/68 |

*Primary Examiner*—Dale R. Ore
*Attorney, Agent, or Firm*—Weingram & Klauber

[57] ABSTRACT

An antiperspirant composition is disclosed suitable for application by a pump spray, a pressurized aerosol or a roll-on. The composition comprises an active antiperspirant salt; a hydrophobic suspending agent; and as a liquid carrier, the benzoic acid esters of a mixture of linear primary alcohols in the $C_9$ to $C_{15}$ carbon chain length. When the said composition is maintained in a pressurized spray container, a liquified normally gaseous propellant is also present. Quantities of additional components may also be present in the composition including ethanol, or other polar solvent such as a fatty acid ester, and a volatile silicone. The said composition exhibits very slow settling times, fast onset of efficacy, and the cited carrier is virtually odor-free.

12 Claims, No Drawings

4,278,655

ANTIPERSPIRANT COMPOSITION

BACKGROUND OF INVENTION

This invention relates generally to antiperspirant compositions, and more specifically relates to an antiperspirant spray composition which is suitable for application by a pump spray or as an aerosol, i.e., by being dispensed from a pressurized aerosol container.

Antiperspirant compositions, particularly those suitable for application as an aerosol spray, commonly include one or more active antipersirant salts together with a suspending agent such as a colloidal silica or a hydrophobic montmorillonite clay, e.g. hydrophobic bentonites such as dimethyl-distearyl-ammonium chloride-treated bentonite, e.g. Bentone 38 or 27, and a liquid carrier. Among the active antiperspirant salts utilized in the said compositions are basic aluminum chlorohydrate (sometimes referred to as aluminum chlorohydroxide); aluminum sulfate; aluminum chloride; aluminum bromides; zirconyl chloride; zirconyl hydroxides; complexes of aluminum hydroxide, zirconyl chloride and aluminum chlorhydroxides; complexes of dihydroxyaluminum glycinate, zirconyl chloride and/or zirconyl hydroxide and aluminum chlorohydroxides; complexes of zirconyl chloride and/or zirconyl hydroxides with aluminum chlorohydroxides and an amino acid such as glycine (as a buffering agent), and mixtures of the foregoing.

Additional agents may also be present as are known in the art, including a small quantity of a polar solvent such as ethanol and/or water which serves to activate the bentonite or other suspending agent; and if the said composition is to be incorporated into an aerosol spray, i.e., within a pressurized container for spray application, then additionally a propellant is provided which is liquified at the pressures maintained within the storage container, but is gaseous at ambient conditions, i.e., upon spraying of the composition. Such propellants may be of various types known in the art including, e.g., a number of well known hydrocarbon propellants such as propane; 2-methyl propane (isobutane); n-butane; and cyclobutane. Various halogenated hydrocarbon propellants are also known for this use such as chlorodifluoromethane; dichlorodifluromethane; and various other halogenated compounds of this type. The propellant can also be a mixture of liquified normally gaseous propellant and a compressed gas such as nitrogen, carbon dioxide, nitrous oxide, etc. Reference may be usefully had in the above connection to the work *Pressurized Packaging (Aerosols)* by Herzka and Pickthall, Academic Press, Inc., New York, N.Y. (1958).

In the past various liquid carriers have been used in the antiperspirant compositions as aforementioned. Among the said carriers which have such found application have been propylene glycol, cetyl alcohol, diethylene glycol, ethyloxylated lanolin, polyoxyethylene ethers, polyoxyethylene sorbitol, lanolin glycerine, steryl alcohol, isopropyl palmitate, and especially isopropyl myristate (IPM). Of the foregoing carriers those that have found particularly wide application are isopropyl palmitate, and especially isopropyl myristate. In practice, however, these last compounds have been found to be less than admirably suited for the purposes for which they been so applied. The said carrier should, e.g., be an oil with relatively good hydrophilic properties, this in order to promote the onset of efficacy by not interfering with the entrance into solution of the active aluminum salt upon initial development of perspiration by the individual utilizing the antiperspirant composition. The aforementioned isopropyl myristate is relatively inferior in this regard.

Additionally, compositions such as the aforementioned IPM, can when sprayed or otherwise applied upon an individual utilizing same, leave a residue which to the touch is oily or greasy—which is aesthetically and practically an undesirable characteristic. Further it may be pointed out that in the case of the previously favored carrier agents, including IPM, the said agents upon chemical breakdown—such as can occur, by oxidation subsequent to application of the compositions to the body—result in breakdown products, which are various fatty acids, such as myristic acid, which products are noteworthy for their disagreeable odor.

In addition to the aforementioned prior art carriers, it has in recent years been proposed that volatile silicones be utilized for the aforementioned purposes. The said silicones are in a number of respects advantageous, e.g., they display relatively good hydrophilic properties, and slowly volatilize at body temperatures thereby allowing body moisture to solubilize the active antiperspirant salt present. Among other objections to the same, however, is the comparatively very high cost of these agents.

In accordance with the foregoing, it may be regarded as an object of the present invention, to provide an antiperspirant composition suitable for application by spray as, e.g., through a spray pump or by an aerosol spray or other dosage forms, which composition is relatively odor-free; which composition when applied on the skin has little or no greasy or oily feel, and produces little or no odor.

It is a further object of the present invention, to provide an antiperspirant composition of the foregoing character, having very high settling time following agitation of same; which upon settling produces a soft pack in the settled layer of solid materials; and which provides a rapid onset of efficacy due to the nature of the carrier.

SUMMARY OF INVENTION

Now in accordance with the present invention, the foregoing objects, and others as will become apparent in the course of the ensuing specification, are achieved in an antiperspirant composition comprising a recognized active antiperspirant salt; a particulate suspending agent; and as a liquid carrier, the benzoic acid esters of a mixture of linear primary alcohols in the $C_9$ to $C_{15}$ carbon chain length. If the said composition is to used by pressurization in a aerosol container then a liquified normally gaseous propellant or mixture of a liquified normally gaseous propellant and a compressed gas, of the types previously discussed, may also be present. If the composition without addition of the said propellant is regarded and designated a "concentrate," then in a typical aerosol formulation the propellant typically comprises from about 40 to 90%, and can comprise as low as 10 to as much as 95% by weight of the total of concentrate and propellant provided to the pressurized can.

The antiperspirant salt, which preferably comprises an aluminum salt such as aluminum chlorhydrate, and which may also comprise the other salts previously referred to, will typically constitute from about 5 to 40% and preferably comprise from about 10 to 25% by weight of the aforementioned concentrate. The particulate suspending agent, which preferably comprises bentonite or an organic derivative of same, or which may comprise other particulate suspending agents such as a pyrogenic colloidal silica, will generally be present in a range from about 0.1% to 10% by weight of the concentrate, and preferably between 0.1% and 7.5%. Mixtures of a hydrophobic montmorillonite clay and a colloidal silica may also be employed as a suspending agent.

A polar solvent, such as propylene carbonate or ethyl alcohol/water (95%/5% by weight) may in addition be present in weight percent of 30 to 75% based on the weight of the hydrophobic clays. The said ethanol is well-known in the present art to activate the suspending agent such as bentonite, i.e., to aid in opening up the platelets of the clay.

The liquid carrier of the present composition will typically be present and range from about 50 to 80 percent by weight of the components in the said concentrate.

In accordance with another aspect of the present invention it has been found that where the benzoate esters above discussed are utilized in conjunction with a volatile silicone, with the weight ratio of the esters to the silicone being in the range of from about 99:1 to 0.1:99.9, and relatively optimally in the ratio of 1:1, unusual synergistic results are achieved. More particularly it has been found as one aspect of the present invention that use of the aforementioned benzoate esters results in very substantial improvements in settling times, i.e., the period necessary for the suspended solid matter to resettle after agitation is markedly increased vis-a-vis prior art carriers such as isopropyl myristate. However when the said combination of the benzoate esters with a volatile silicone is employed, an unusual and surprising further increase in suspension time, i.e., in settling time, results—such that the settling time far exceeds that obtained by use of either of the two components alone as a carrier.

The benzoate ester carriers utilized in the present invention have been disclosed in the copending patent application of Thomas L. Scala, Jr. which was filed on Oct. 10, 1978, under U.S. Ser. No. 949,630, and is entitled "Improved Ester Compositions," the said application being assigned to the assignee of the instant application, now abandoned.

These organic liquid compositions generally comprise the benzoic acid esters of mixtures of linear primary alcohols in the $C_9$ to $C_{15}$ carbon chain length range. These benzoates are the reaction products of benzoic acid with mixtures of the aforementioned linear primary alcohols. Preferably the alcohol mixture includes one or more said alcohols of odd-numbered chain length, and one or more said alcohols of even-numbered chain length. Thus, for example, the mixture of such alcohols utilized in preparing these benzoates may comprise one of the $C_9$ to $C_{11}$ said alcohols, of the $C_{12}$ and $C_{15}$ said alcohols, of the $C_{12}$ and $C_{13}$ said alcohols, of the $C_{14}$ and $C_{15}$ said alcohols, of the $C_{12}$ through $C_{15}$ such alcohols, etc. The one or more odd numbered alcohols are typically present in the alcohol mixture in the range from about 30 to 70 percent by weight, with the balance being the one or more said even numbered alcohols.

Mixtures of the aforementioned odd and even-numbered linear primary alcohols utilizable in preparing the benzoate products utilized herein are available from the Shell Chemical Co., Industrial Chemicals Division, New York, N.Y., under the registered trademark NEODOL. Among the said products which may be utilized in preparing the composition of the benzoates utilized herein are NEODOL 23, which is a mixture of $C_{12}$ and $C_{13}$ linear primary alcohols; and NEODOL 25, which is a mixture of $C_{12}$, $C_{13}$, $C_{14}$, and $C_{15}$ of such alcohols; NEODOL 45, which is a mixture of $C_{14}$ and $C_{15}$ of such alcohols; and NEODOL 91, which is a mixture of $C_9$, $C_{10}$, and $C_{11}$ of such alcohols.

The said esters utilizable herein, may also be prepared by reaction with benzoic acid of a mixture of two or more even-numbered linear primary alcohols, as for example the ALFO 1214 product of Conoco Chemical Co. which product is a mixture of the $C_{12}$ and $C_{14}$ of said alcohols.

Antiperspirant compositions in accordance with the present invention, and thus utilizing the benzoate liquid carriers aforementioned, either alone or in combination with a volatile silicone, are found to have markedly superior characteristics in comparison to prior art antiperspirant compositions intended for similar uses. The aforementioned benzoates are characterized among other things by strikingly low odor, which is a generally a most desirable characteristic for the present purposes. The absence of odor also pertains to the breakdown products of these esters, which can result subsequent use of same, e.g., by oxidation at the body surface. The resultant oxidation products are thus also innocuous and odor-free.

The carriers of the invention, further, for reasons that are not completely understood, produce in the antiperspirant product prepared with same, very superior properties as respects settling times of the agitated antiperspirant composition, as well as more rapid onset of efficacy. In addition, and as indicated previously, when a combination of the benzoates and a volatile silicone is employed, yet further improvement in settling times is evidenced; a very clear synergistic effect is seen to occur, in that the settling time exceeds that obtainable with either of the carrier components when used alone.

Compositions in accordance with the invention are further characterized by a marked absence of oily or greasy feel when same are deposited upon the skin surface, which is an important characteristic for aesthetic reasons, and for consumer acceptance of the same.

DESCRIPTION OF THE PREFERRED EMBODIMENTS

The invention is further illustrated by the following Examples, wherein Examples I and II are prior art compositions, and Example III is a control formulation. It will of course be understood that the said Examples are intended to be illustrative, and not delimitive of the invention:

EXAMPLE I

In this Example a prior art aerosol antiperspirant composition was prepared, which utilized isopropyl myristate as a carrier. The formulation of the composition was as follows:

| Component | % by weight |
|---|---|
| Bentone 38* | 0.7 |
| ethanol** | 0.7 |
| isopropyl myristate | 16.2 |
| aluminum cholorhydrate+ | 5.9 |

| Component | % by weight |
|---|---|
| propellant++ | 76.5 |

*trademark of National Lead Co. for organic derivatives of hydrous magnesium aluminum silicate minerals, utlized here as a particulate suspending agent.
**SDA-40 grade, 95%.
+composition utilized was the "Micro-Dry" product of Reheis Chemical Co., which is a 5/6 basics formulation.
++"Propellant A-46" of Philips Petroleum Co., which is a blend of isobutane, butane and propane.

This conventional composition when sprayed upon the skin left a relatively oily feeling residue. When the composition was agitated, it took approximately 150 seconds for settling of the suspended matter.

EXAMPLE II

In this Example a further prior art aerosol composition was prepared, utilizing a volatile silicone as a carrier, i.e., in place of isopropyl myristate. The formulation of the composition were as follows, where the components other than the volatile silicone are as identified in Example I:

| Component | % by weight |
|---|---|
| Bentone 38 | 0.7 |
| ethanol | 0.7 |
| volatile silicone* | 16.2 |
| aluminum chlorohydrate | 5.9 |
| propellant | 76.5 |

*composition utilized was SWS 03314, a volatile cyclic silicone oil which is a product of SWS Silicones Corp. of Adrian, Michigan, and which may be represented by the formula

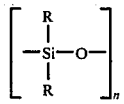

where R is a 1 to 3 carbon alkyl group and preferably a methyl group, and n is a number from 3 to about 10 and preferably from 3 to 7, which are then joined together to form a cyclic structure.

The volatile silicone provides certain advantages to the composition of this Example—vis-a-vis the composition of Example I. The present composition when sprayed upon the skin, e.g., leaves a less oily-feeling residue. Moreover onset of efficacy is more rapid with this composition because the silicone is less hydrophobic than is the IPM. On the other hand it was found that following agitation of this composition, it took approximately 50 seconds for settling of the suspended matter. Such rapid settling is quite undesirable since uniformity of the suspension is desired for a relatively long period in order to maintain uniformity during use, from use to use, and to avoid clogging of the aerosol valve etc.

EXAMPLE III

For purposes of providing control data for comparison to aspects of the present invention, a further aerosol antiperspirant composition was prepared, wherein a combination of isopropyl myristate and a volatile silicone was used as a carrier. The formulation of this further composition was as follows, where all components are as identified in Examples I and II:

| Component | % by weight |
|---|---|
| Bentone 38 | 0.7 |
| ethanol | 0.7 |
| isopropyl myristate | 8.0 |
| volatile silicone | 8.2 |
| aluminum chlorohydrate | 5.9 |
| propellant | 76.5 |

The above composition was found to require approximately 100 seconds for settling following agitation.

EXAMPLE IV

In this Example an aerosol antiperspirant composition pursuant to the invention was prepared, wherein the carrier comprised a mixture of benzoic acid esters as previously described. The formulation of the composition was as follows, where the components, other than the said esters, are in accordance with the identification provided in Example I through III:

| Component | % by weight |
|---|---|
| Bentone 38 | 0.7 |
| ethanol | 0.7 |
| benzoate esters* | 16.2 |
| aluminum chlorohydrate | 5.9 |
| propellant | 76.5 |

*The benzoate esters utilized in this Example were the reaction products of benzoic acid with the NEODOL 25 product of Shell Chemical Co. NEODOL 25 is a mixture by weight of 24% of $C_{12}$ linear primary alcohol, with 28% of $C_{13}$, 32% of $C_{14}$ and 16% of the $C_{15}$ such alcohols.

The composition of this Example when sprayed upon the skin, left a residue that was neither oily or greasy to the touch; and such residue was odor-free. Onset of efficacy was more rapid with this composition than with that of Examples I and III. Following agitation of the composition, approximately 160 seconds were required for settling of the suspended matter. In addition the packing of the settled matter was "soft," which is a desirable characteristic in that subsequent agitation is then able to readily resuspend the particulate matter.

EXAMPLE V

In this Example a further aerosol antiperspirant composition pursuant to the invention was prepared, wherein the carrier comprised the benzoic acid esters as in Example IV, which were however mixed with a volatile silicone of the type described in Examples II and III. The formulation of the compositions was as follows, where the several compounds are all as identified in the previous Examples:

| Component | % by weight |
|---|---|
| Bentone 38 | 0.7 |
| ethanol | 0.7 |
| benzoate esters | 8.0 |
| volatile silicone | 8.2 |
| aluminum chlorohydrate | 5.9 |
| propellant | 76.5 |

The composition of this Example, when sprayed upon the skin, exhibited all of the positive properties of the Example IV composition. It was unexpectedly found, further, that the present composition, following agitation, took approximately 250 seconds for settling of the suspended matter. Comparison with Examples II and IV will render clear the synergistic action that has occurred. Thus in Example II where the volatile silicone is used alone, the settling time was 50 seconds; and where in Example IV the benzoate esters are used as the sole carriers, settling time was 150 seconds.

While the present invention has been set forth in terms of specific embodiments thereof, it will be understood in view of the present disclosure, that numerous variations are now enabled to those skilled in the art, which variations yet reside within the scope of the instant teaching. Accordingly, the invention is to be broadly construed, and limited only by the scope and spirit of the claims now appended hereto.

I claim:

1. In an antipersipirant composition comprising an active antiperspirant salt, a particular suspending agent, and a liquid carrier, the improvement comprising wherein said liquid carrier comprises the benzoic acid esters of a mixture of linear primary alcohols in the $C_9$ to $C_{15}$ carbon chain length range, said esters enabling increased suspension time and softer packing of settled matter following agitation of said composition, and a reduction in odor and in oily sensation when said composition is deposited upon the skin.

2. A composition in accordance with claim 1, wherein said composition is maintained in a pressurized spray container, together with a propellant.

3. A composition in accordance with claim 1, wherein salt comprises from about 5 to 40 percent by weight thereof, and said carrier comprises 30 to 90 percent by weight thereof.

4. A composition in accordance with claim 3, wherein said suspending agent comprises from about 0.1 to 10% by weight of said composition.

5. A composition in accordance with claim 2, wherein said propellant comprises from about 40 to 90 percent by weight of the contents of said container.

6. In an antiperspirant composition comprising an active antiperspirant salt, a particulate suspending agent, and a liquid carrier, the improvement comprising wherein said liquid carrier comprises a mixture of (a) the benzoic acid esters of a mixture of linear primary alcohols in the $C_9$ to $C_{15}$ carbon chain length range with (b) a volatile silicone, said esters enabling increased suspension time and softer packing of settled matter following agitation of said composition, and a reduction in odor and in oily sensation when said composition is deposited upon the skin.

7. A composition in accordance with claim 6, wherein said salt is an aluminum salt.

8. A composition in accordance with claim 6, wherein the ratio between said benzoic acid esters and said silicone is in the range of from about 99:1 to 1:99.

9. A composition in accordance with claim 6, wherein said salt comprises from about 5 to 40 percent by weight of said composition, and said carrier comprises from about 50 to 80 percent by weight thereof.

10. A composition in accordance with claim 6, wherein said composition is maintained in a pressurized container; together with a propellant; said propellant comprising 40 to 90 percent by weight of the contents of said container.

11. A composition in accordance with claim 1, wherein said benzoic acid esters are those of a mixture of linear primary alcohols in the $C_{12}$ to $C_{15}$ carbon chain length range.

12. A composition in accordance with claim 6, wherein said benzoic acid esters are those of a mixture of linear primary alcohols in the $C_{12}$ to $C_{15}$ carbon chain length range.

* * * * *

UNITED STATES PATENT OFFICE
CERTIFICATE OF CORRECTION

Patent No. 4,278,655     Dated July 14, 1981

Inventor(s) Steele J. Elmi

It is certified that error appears in the above-identified patent and that said Letters Patent are hereby corrected as shown below:

Col. 7, Claim 1, Line 2

"particular" should read --particulate--

Signed and Sealed this

Tenth Day of August 1982

[SEAL]

Attest:

Attesting Officer

GERALD J. MOSSINGHOFF
Commissioner of Patents and Trademarks